United States Patent [19]
Mishima et al.

[11] Patent Number: 6,159,191
[45] Date of Patent: Dec. 12, 2000

[54] DISPOSABLE DIAPER HAVING LEAKAGE PREVENTING WALLS

[75] Inventors: Yoshitaka Mishima; Yasushi Sayama, both of Kagawa-ken, Japan

[73] Assignee: Uni-Charm Corporation, Japan

[21] Appl. No.: 09/160,659

[22] Filed: Sep. 25, 1998

[30] Foreign Application Priority Data

Sep. 30, 1997 [JP] Japan .................................. 9-265637

[51] Int. Cl.7 .................................................. A61F 13/15
[52] U.S. Cl. .......................... 604/385.28; 604/385.29; 604/391; 604/394
[58] Field of Search ...................... 604/385.1, 385.2, 604/386, 387, 391–402, 385.01, 385.24–385.3

[56] References Cited

U.S. PATENT DOCUMENTS

| | | |
|---|---|---|
| 5,133,371 | 7/1992 | Sivess . |
| 5,653,843 | 8/1997 | Fell et al. ............................. 604/385.2 |

FOREIGN PATENT DOCUMENTS

| | | |
|---|---|---|
| 0 346 477 | 12/1989 | European Pat. Off. . |
| 64-68503 | 3/1989 | Japan . |
| 1-168903 | 7/1989 | Japan . |
| 2 263 622 | 8/1993 | United Kingdom ................ 604/385.2 |
| 96/07381 | 3/1996 | WIPO . |
| 97/21409 | 6/1997 | WIPO . |

*Primary Examiner*—John G. Weiss
*Assistant Examiner*—K. M. Reiche
*Attorney, Agent, or Firm*—Baker & Daniels

[57] ABSTRACT

A disposable diaper which includes a pair of leakage preventing walls extending side by side longitudinally of the diaper. The top of each of the leakage preventing walls is provided with a 20~100 mm wide cushion pad having an elastic stretchability in a longitudinal direction of the diaper and an elastic contractility in a thickness direction of the diaper. The cushion pads are normally biased to contract longitudinally of the diaper.

5 Claims, 3 Drawing Sheets

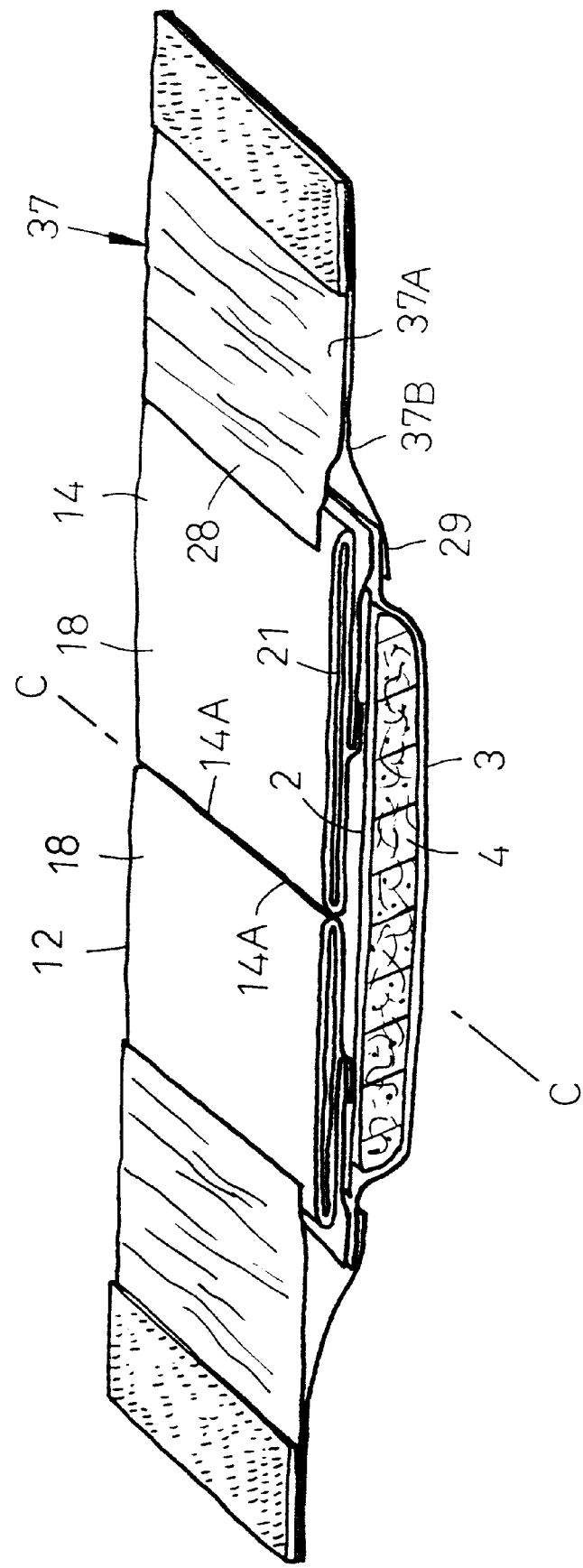

DISPOSABLE DIAPER HAVING LEAKAGE PREVENTING WALLS

BACKGROUND OF THE INVENTION

This invention relates to disposable diapers and more particularly to diapers which have a pair of leakage preventing walls which provide a good fit to the wearer's body.

Japanese Patent Application Disclosure (Kokai) No. Sho64-68503 discloses a disposable diaper provided with leakage proofing means that including flexible flaps and elastic members. The flaps include a first branched portion extending upward from an inner side of the diaper, a second branched portion extending inward from the first branched portion and a third branched portion extending outward from the first branched portion. The elastic members are provided on the second and third branched portions.

The leakage proofing means in the above-mentioned diaper are adapted to be placed against the wearer's skin along the first and second branched portions which are relatively flat. To achieve a high leakage proofing effect with the means disclosed in this prior art, a stretch stress of the elastic member must be sufficiently high to ensure a desired fit to the wearer's body. This because is the respective branched portions are configured to be relatively flat. However, an excessively high stretch stress may interrupt blood circulation and/or cause irritation to the wearer's skin and consequently create a feeling of discomfort for the wearer. This known diaper does not include a leakage proofing means that can be utilized to form an excretion holding pocket which protects the wearer's skin from contact with excretion held in such a pocket.

SUMMARY OF THE INVENTION

It is an object of the invention to provide a disposable diaper having a pair of leakage preventing walls adapted to fit a wearer's body and to achieve a high leakage proofing effect without requiring an excessively tight-fit. It is another object of the invention to utilize the leakage preventing walls to form an excretion holding space or pocket so that the wearer's skin can be effectively protected from being stained with excretion held in the space or pocket.

According to the invention, there is provided a disposable diaper having a front waist region, a rear waist region and a crotch region extending in a longitudinal direction of said diaper therebetween. The diaper comprises a liquid-permeable topsheet, a liquid-impermeable backsheet, a liquid-absorbent core disposed therebetween, and a pair of leakage preventing walls adapted to rise up on an inner surface of said diaper when said diaper is worn. The pair of leakage preventing walls have tops thereof defined by a pair of 20~100 mm wide cushion pads. Each cushion pad has an elastic stretchability in the longitudinal direction and an elastic contractility in a thickness direction of said diaper.

According to an embodiment of the invention, each of the cushion pads comprises tube-shaped covering member made of hydrophobic nonwoven fabric, an elastic member bonded to an inner surface of the covering member under a tension in the longitudinal direction and a cushioning member composed of plural crimped filaments arranged inside the covering member so as to extend in parallel one to another in the longitudinal direction.

According to another embodiment of the invention, the cushioning member comprises filaments having a fineness of 0.5~10 deniers and occupies 30~80% of a cross-sectional area defined by the covering member.

According to still another embodiment of the invention, there are further provided a pair of elastic wings extending outward from transversely opposite side edges of the rear waist region each having an elastic stretchability in a transverse direction of the diaper and comprising first and second elastic wings lying on inner and outer sides of the diaper, respectively. The first and second elastic wings have distal ends thereof bonded together. At proximal ends of the first and second elastic wings, the first elastic wing is at least partially bonded to the associated one of the cushion pads, and the second elastic wing is bonded to an outer surface of the rear waist region along the associated side edge thereof.

According to another further embodiment of the invention, inner side edges of the respective cushion pads are spaced from each other by 0~20 mm in the crotch region.

BRIEF DESCRIPTION OF THE DRAWINGS

FIG. 3 is a fragmentary perspective view of the partly cutaway diaper in a section taken along a line III—III in FIG. 1.

DESCRIPTION OF THE PREFERRED EMBODIMENTS

Details of a disposable diaper according to the invention will be more fully understood from the description given hereunder with reference to the accompanying drawings.

Figure 1:
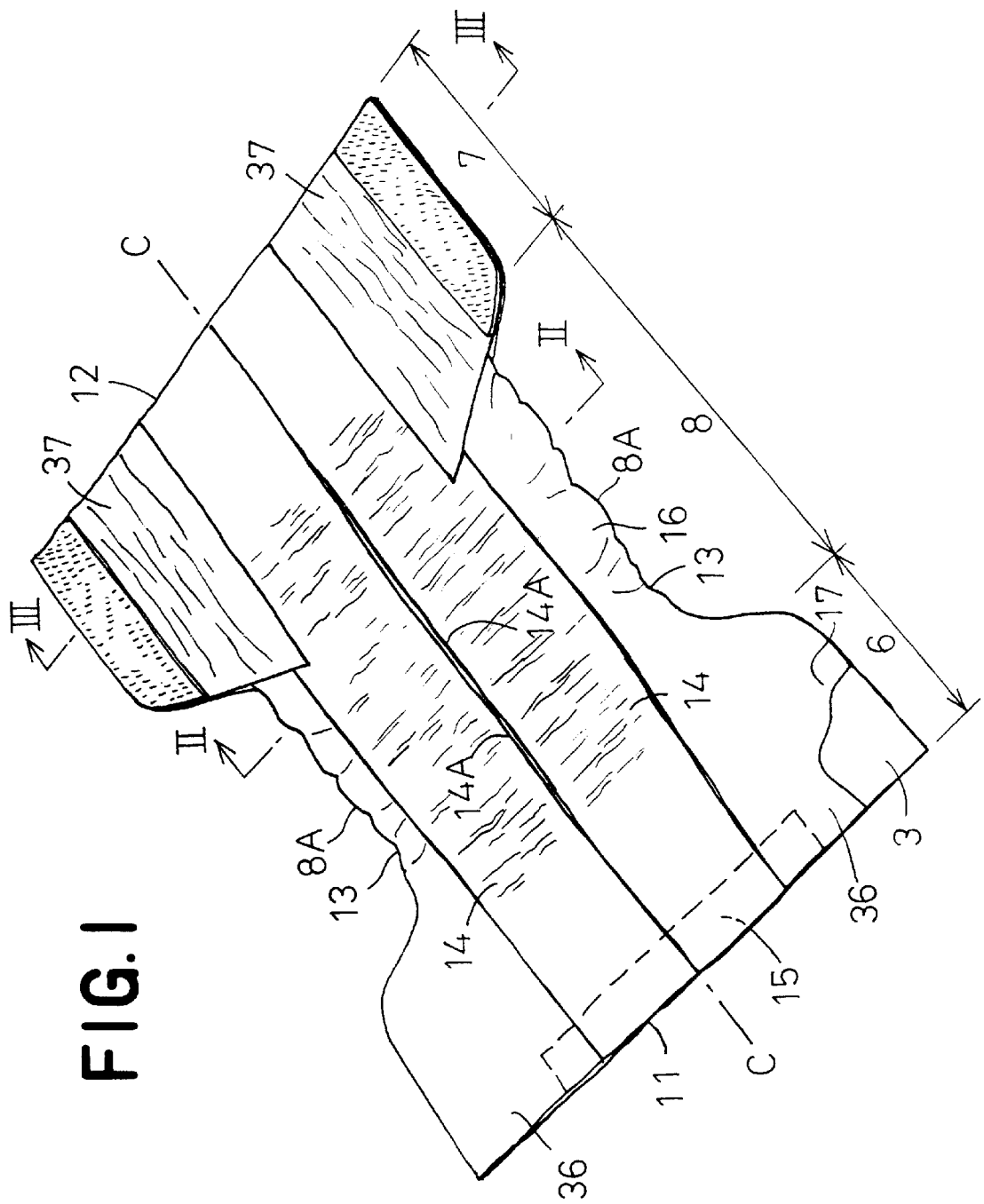
FIG. 1 is a perspective view of an embodiment of a partly cutaway disposable diaper according to the invention.
Figure 2:
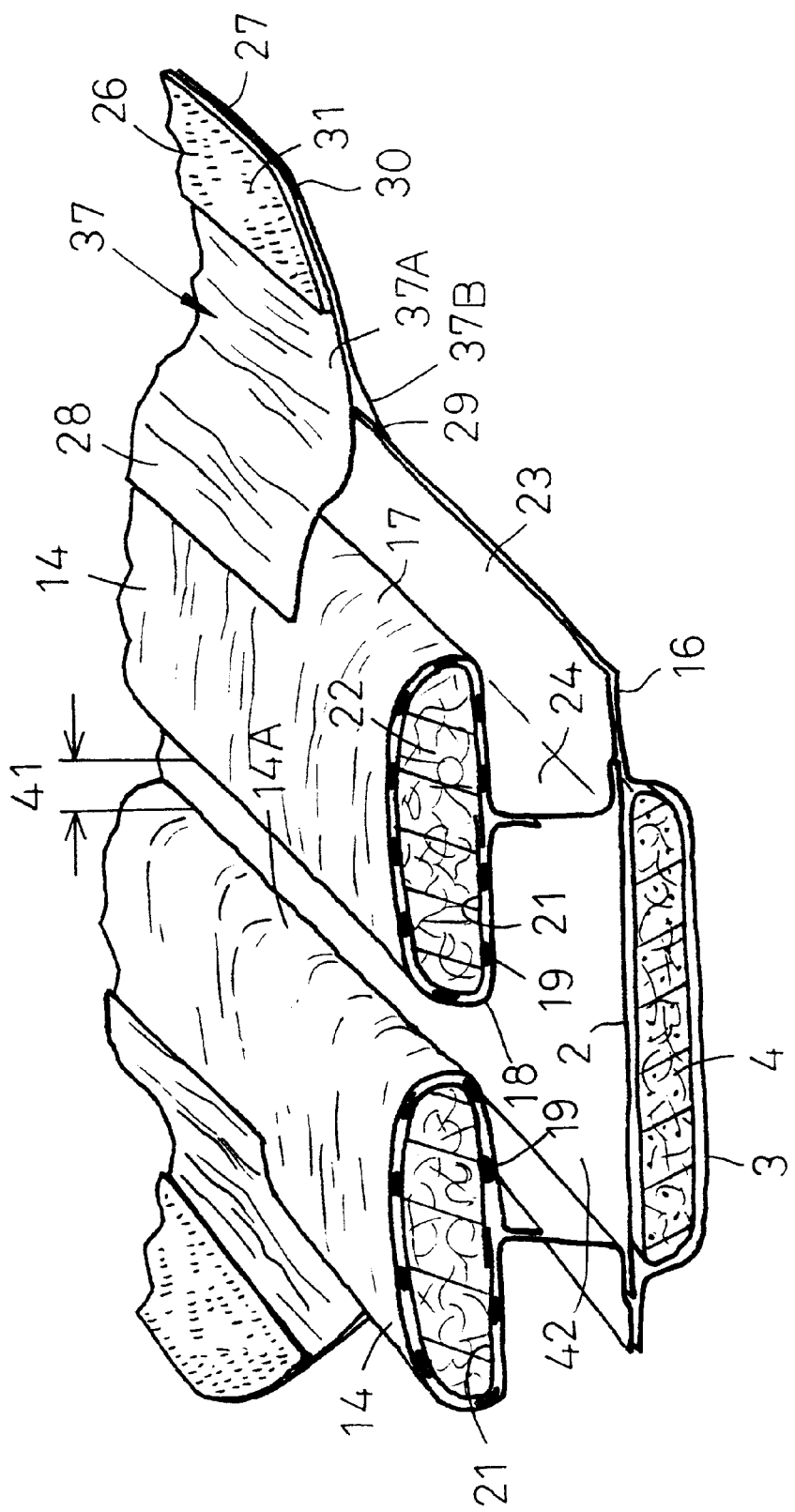
FIG. 2 is a fragmentary perspective view of the partly cutaway diaper in a section taken along a line II—II in FIG. 1.

FIGS. 1, 2 and 3 depict a diaper according to the invention in a partly cutaway perspective view, and partly cutaway in fragmentary perspective views in sections taken along lines II—II and III—III, respectively, in FIG. 1. It should be understood that FIG. 2 shows the diaper as curved inward along its longitudinal direction with cushion pads 14 contracting.

Referring to these figures, the diaper is composed of a liquid-permeable topsheet 2, a liquid-impermeable backsheet 3 and a liquid-absorbent core 4. The diaper has a front waist region 6, a rear waist region 7 and a crotch region 8 extending between these waist regions 6, 7 as viewed longitudinally. The front and rear waist regions 6, 7 respectively have a pair of front wings 36, 36 and a pair of rear wings 37, 37 extending outward beyond transversely opposite side edges 8A, 8A of the crotch region 8, respectively. The diaper presents, in its unfolded state, a substantially hourglass-shape defined by longitudinally opposite ends 11, 12 and transversely opposite side edges 13, 13. The diaper is provided on its inner side with a pair of cushion pads 14, 14 extending in parallel to and symmetrically with respect to a longitudinal center line C—C between the longitudinally opposite ends 11, 12. The pair of cushion pads 14, 14 are elastically stretchable in their longitudinal direction and may be dimensioned so as to cover most of the inner side of the diaper except the front and rear wings 36, 36, 37, 37. Inner side edges 14A, 14A of the cushion pads 14, 14 may be arranged so as to be in contact with each other or slightly spaced from each other. In the front waist region 6, an elastic member 15 made of foamed urethane rubber extends along the front end 11 and is bonded under appropriate tension to the inner surface of the topsheet 2 and/or the backsheet 3.

As will be apparent from FIG. 2, the absorbent core 4 is disposed between the topsheet 2 and the backsheet 3 which extend outward beyond peripheral edges of the absorbent core 4. Along these extensions, the topsheet 2 and the backsheet 3 are placed one upon another and bonded together by means of hot melt adhesive (not shown). The backsheet 3 further extends outward beyond transversely opposite side edges of the topsheet 2 to form a pair of side flaps 16 at least in the crotch region 8.

Each of the cushion pads 14 is composed of a tube-shaped covering member 18 formed of a hydrophobic sheet 17, a stretchable elastic member 21 bonded intermittently to the entire inner surface of the covering member 18 by means of hot melt adhesive 19 and a cushioning member 22 formed by filaments, preferably crimped filaments. The cushion pads 14 have widths of 20~100 mm in the crotch region 8 and in the proximity thereof. The hydrophobic sheet 17 extends from the covering member 18 to the inner surface of the diaper and its distal end 23 is folded outward of the diaper. The distal end 23 is bonded to an upper surface of the topsheet 2 by means of hot melt adhesive (not shown). The distal end 23 further extends outward and is bonded also to an upper surface of the side flap 16. A portion of the hydrophobic sheet 17 extending between the covering member 18 and the upper surface of the topsheet 2 forms a leakage preventing wall 24 adapted to dam up a quantity of body fluids which otherwise flow and leak sideways.

The hydrophobic sheet 17 is made of a relatively bulky and comfortably soft nonwoven fabric of thermoplastic synthetic fiber, preferably of crimped and conjugated fibers. More preferably, the hydrophobic sheet 17 is made of a relatively bulky nonwoven fabric which is elastically stretchable longitudinally of the diaper.

The stretchable elastic member 21 is made of material selected from a group including elastomer sheet, rubber sheet and rubber yarn. The stretchable elastic member 21 is secured to the covering member 18 under appropriate tension directed longitudinally of the diaper so as to make the covering member 18 elastically stretchable/contractile in the longitudinal direction. When a sheet of urethane is employed as an illustrative example of the rubber sheet, preferably the sheet has a thickness of 15~40μ, provides a stress of 400~800 g per unit width of 25 mm as the sheet is stretched by 100% and is secured to the covering member 18 with an elongation of 60~100%.

The filaments forming the cushioning member 22 preferably have a fineness of 0.5~10 d and the amount of filaments used is preferably adjusted so as to occupy 30~80% of the maximum sectional area of the covering member 18. The filaments extend substantially in parallel one to another longitudinally of the diaper and have their length dimensioned so that the respective filaments may have their front and rear ends spaced from the front and rear ends 11, 12 of the diaper by 10~50 mm, respectively. Some of the filaments laid in contact with the inner surface of the covering member 18 may be at least partially bonded to the inner surface. In addition, some of the filaments may have their front and/or rear ends bonded to the inner surface of the covering member 18 or to the elastic member 21.

Each of the rear wings 37 extending outward from the rear waist region 7 is composed of an inner wing 37A and an outer wing, 37B, both of which have an elastic stretchability circumferentially along the wearer's waist. Distal ends 26, 27 of these inner and outer wings 37A, 37B are put flat and bonded together by means of hot melt adhesive 30. A proximal end 28 of the inner wing 37A opposite to the distal end 26 has its inner surface at least partially bonded to an upper surface of the cushion pad 14 by means of adhesive (not shown) while a proximal end 29 of the outer wing 37B has its inner surface bonded to an outer surface of the diaper. These inner and outer wings 36A, 37B are spaced from each other except at their distal ends 26, 27. The distal end 26 of the outer wing 37B has its inner surface provided with a male member 31 of the mechanical fastener commonly known under the trade mark VELCRO.

As will be readily understood from FIG. 3, the covering member 18 does not contain any of the cushioning member 22 in the vicinity of the rear end 12 of the rear waist region 7. The covering member 18, said elastic member 21 and said topsheet 2 are put flat and bonded together by means of adhesive (not shown). The inner side edges 14A of the pair of cushion pads 14 contact each other along the center-line or may be slightly spaced apart from each other. The configuration of the cushion pad 14 in the front waist region 6 is substantially similar to that in the rear waist region 7. It should be understood, however, that the configuration of the front wing 36 in the front waist region 6 is similar to that of the flap 16 in the crotch region, i.e., the front wing 36 is composed of the backsheet 3 and the hydrophobic sheet 17 bonded thereto, as will be apparent from FIG. 1.

The diaper constructed as described hereinabove is put on the wearer's body by pulling the rear wings 37 circumferentially around the wearer's waist, placing these rear wings 37 against outer sides of the respective front wings 36 and fastening the male members 31 to the corresponding female members (not shown) provided on an outer surface of the front waist region 6. Pulling the rear wings 37 in the manner as described above causes the pair of cushion pads 14 to be moved sideways and thereby be spaced from each other so as to form a clearance 41 adapted to receive excretion discharged on the diaper. Curving the diaper inward along its longitudinal direction, i.e., along the wearer's crotch region with the topsheet 2 inside causes the cushion pads 14 to be spaced upward from the inner surface of the diaper under contractile effect of the elastic member 21. As the cushion pads 14 are moved upward to their positions above the topsheet 2, the leakage preventing walls 24 rise up on the inner surface of the diaper. The leakage preventing walls 24 cooperate with the respective cushion pads 14 to form a space or pocket 42 on the inner surface of the diaper which receives and holds excretions (See FIG. 2). The cushion pads 14 cover the space or pocket 42 except for clearance 41 to avoid an apprehension that the wearer's skin might be stained with excretions held in the space or pocket 42. Such an arrangement of the cushion pads 14 is preferable not only from the viewpoint of sanitation but also appearance, since the interior of the space 42 holding therein excretions is substantially covered with the cushion pads 14.

Each of the cushion pads 14 is relatively wide and soft. Additionally, the filaments constituting the cushioning member 22 are deformable so as to follow the wearer's body curve and movable at least transversely within the covering member 18. These factors allow the cushion pads 14 to fit the wearer's skin over a relatively large area and thereby prevent leakage of urine or soft passage from occurring due to a noticeable gap between the pads 14 and the skin even if the pads 14 are not tightly placed against the skin.

The invention is not limited to the illustrated embodiment but can be implemented in the other various manners without departing from the scope of the invention. For example, the front wing 36 may be composed of a pair of stretchable wings as in the case of the rear wing 37. If the rear wings are dimensioned to be relatively large circumferentially around the wearer's waist, the front wings 36 can be eliminated. The inner side edges 14A of the respective cushion pads 14 may be more or less spaced from each other so long as the diaper is in its unfolded state as shown by FIG. 1. It should be understood that a distance by which these inner side edges 14A may be spaced apart from each other is preferably less than 20 mm in the crotch region 8. Bonding of the diaper components may be achieved by means of a suitable adhesive agent such as hot melt adhesive or by means of heat-sealing when the components to be bonded together are of a heat-sealable nature.

In the disposable diaper provided by the invention, the tops of the respective leakage preventing walls are defined by a pair of the cushion pads each having a relatively large width. These cushion pads are elastically stretchable longitudinally of the diaper, on one hand, and elastically contractile in the direction of their thickness. Accordingly, the tops of the respective leakage preventing walls fit along the wearer's skin over a large area and avoid leakage of body fluids even if the tops of the respective leakage preventing walls are not tightly placed against the skin.

The cushioning member of the cushion pads is composed of a plurality of filaments extending in parallel one to another longitudinally of the diaper. The individual filaments are deformable and movable so as to follow a curved surface of the wearer as the cushion pads are placed against the wearer's skin. Such a feature advantageously ensures a good fit of the cushion pads to the wearer's skin.

A pair of the cushion pads cooperate with the associated leakage preventing walls to form the excretion holding space or pocket. More specifically, these cushion pads are spaced from each other to form an opening for the space or pocket as a pair of the wings in the rear waist region are pulled in opposite directions circumferentially around the wearer's waist. By adjustably pulling the cushion pads depending on the wearer's body dimensions, the width of the opening can be adjusted in proportion to the body dimensions and the wearer's skin can be protected from being stained with excretion held in the space or pocket.

What is claimed is:

1. A disposable diaper having inner and outer surfaces, front and rear waist regions, and a crotch region extending between the front and rear waist regions, said disposable diaper comprising:

a liquid-permeable topsheet;

a liquid-impermeable backsheet;

a liquid-absorbent core disposed between the liquid-permeable topsheet and the liquid-impermeable backsheet;

a pair of cushion pads coupled to the inner surface of the diaper by a pair of leakage preventing walls that are configured to rise up on the inner surface of the diaper when the diaper is worn, each cushion pad being connected along a lower transversely intermediate portion thereof to a top of a respective one of the pair of leakage preventing walls, each cushion pad having an elastic stretchability along a longitudinal direction of the diaper and an elastic contractility along a thickness direction of the diaper, transversely opposed side edges of each of the pair of cushion pads being spaced apart from each other by a distance of 20 mm to 100 mm; and a pair of rear wings extending outward from transversely opposite side edges of the rear waist region, the pair of rear wings having an elastic stretchability in a transverse direction of the diaper and each comprising first and second elastic wings, that have distal and proximal ends, lying on inner and outer surfaces of the diaper respectively, the distal ends of each pair of the first and second elastic wings being bonded together and the proximal each pair of the first elastic wings being bonded to an adjacent cushion pad, and the proximal end of the each of the second elastic wings being bonded to an outer surface of the rear waist region along an adjacent one of said side edges thereof.

2. The disposable diaper according to claim 1, wherein each of the cushion pads comprise a tube-shaped covering member made of a hydrophobic fabric and having a transversely long elliptical cross-section, an elastic member secured to an inner surface of said covering member under tension in said longitudinal direction, and a cushioning member composed of a plurality of crimped filaments arranged inside the covering member so as to extend in parallel one to another in the longitudinal direction.

3. The disposable diaper according to claim 2, wherein the tube-shaped member is formed from nonwoven sheet of the fabric that extends from the covering member to the inner surface of the diaper to form the leakage preventing walls, the leakage preventing walls being bonded to the inner surface of the diaper.

4. The disposable diaper according to claim 2, wherein the cushioning member comprises filaments having a fineness of 0.5 to 10 deniers and occupying 30 to 80% of a cross-sectional area defined by the tube-shaped covering member.

5. The disposable diaper according to claim 1, wherein the inner ones of said transversely opposed side edges of the cushion pads are spaced apart from one another by a distance of up to 20 mm in the crotch region.

* * * * *